United States Patent [19]
Puyol et al.

[11] Patent Number: 5,491,131
[45] Date of Patent: Feb. 13, 1996

[54] SOMATOSTATIN-ACTIVE POLYPEPTIDE COMPOSITION

[75] Inventors: Manuel R. Puyol; Diego R. Puyol, both of Madrid, Spain

[73] Assignee: Applied Research Systems ARS Holding NV, Curacao, Netherlands Antilles

[21] Appl. No.: 945,836

[22] Filed: Sep. 16, 1992

Related U.S. Application Data

[63] Continuation of Ser. No. 623,943, Dec. 6, 1990, abandoned.

[30] Foreign Application Priority Data

Apr. 14, 1989 [GB] United Kingdom ............ 8908457

[51] Int. Cl.$^6$ ............ A61K 38/00; C07K 7/08; C07K 7/00
[52] U.S. Cl. ............ 514/14; 530/311; 530/327
[58] Field of Search ............ 514/14; 530/311, 530/27

[56] References Cited

U.S. PATENT DOCUMENTS 3,773,919  11/1973  Boswell et al. .
4,728,638  3/1988  Bauer et al. .

OTHER PUBLICATIONS

Remington's Pharmaceutical Science, Mack Publishing Co. 16th Edition, pp. 654–655. 1980.
Limberg, et al, New England Journal of Medicine, vol. 303, No. 5, (1980) 284.
Mountokalakis, et al, Nephrology Dialysis Transplantation, 1988, 3:604–607.
Chemical Abstracts, vol. 103, 1985.
Chemical Abstracts vol. 96, 1982.
Chemical Abstracts vol. 101, 1984.
Chemical Abstracts vol. 97, 1982.
Sizonenko, Endocrinological Control of Growth, Postgrad, Med. J. 1978, Suppl. 1, 91.
Ashton et al–Br. J. Clin. Pharmac. 1976, 3, 523.
Inverson et al, Nature, 1978, 273 161.
Lins et al–Lancet 1978, 2, 687.
John Gerich, Archs. Intern. Med. 1977, 137 659.
G. M. Besser et al–Lancet 1975 1, 1166.
S. E. Christensen et al–Lancet, 1975 1 1426.
Sidman et al, Journal of Membrane Science 7 (1980) 277–291.
Misra, American Journal of Clinical Pathology, pp. 135–139.
S. A. Jenkins et al, Klinische Wochenschrift, 1986, 64, 100–106.
Thomas G. Murray et al, J. Int. Med. Res (1981) 9, 1.
P. N. Maton et al, The New England Journal of Medicine, vol. 312, No. 1, (1985) 17–21.
Creutzfeldt et al, World J. Surg., vol. 5, No. 3, 341–350 (1981).
R. Lugari et al, Proc. EDTA–ERS, vol. 21, 1984, pp. 614–617.
Halma et al, Annals of Internal Medicine, vol. 107, No. 4 (1987) pp. 518–520.

*Primary Examiner*—Jill Warden
*Assistant Examiner*—S. G. Marshall
*Attorney, Agent, or Firm*—Foley & Lardner

[57] ABSTRACT

Pharmaceutical compositions for use in the prevention or treatment of diseases and dysfunctions associated with pathological contraction of mesangial cells and other contractile cells responsive to angiotensin II and/or oxygen free radicals, comprise as an active ingredient one or more somatostatin-active polypeptides. The somatostatins are particularly useful for the treatment or prevention of renal dysfunction.

13 Claims, 15 Drawing Sheets

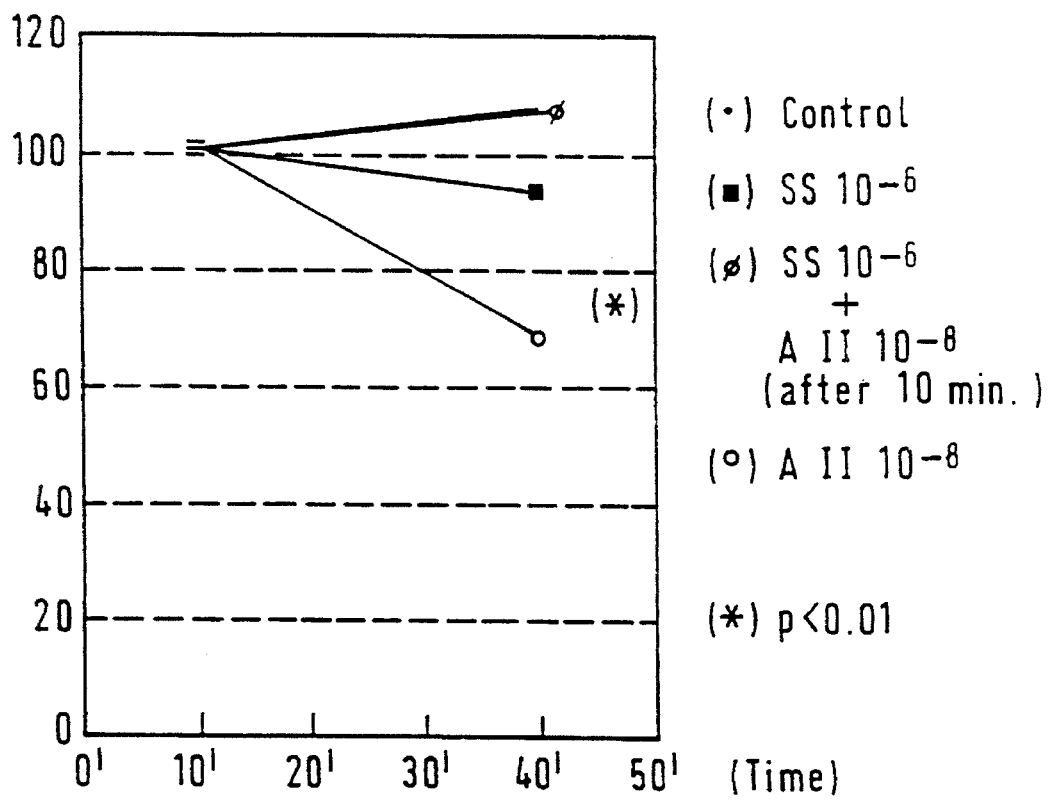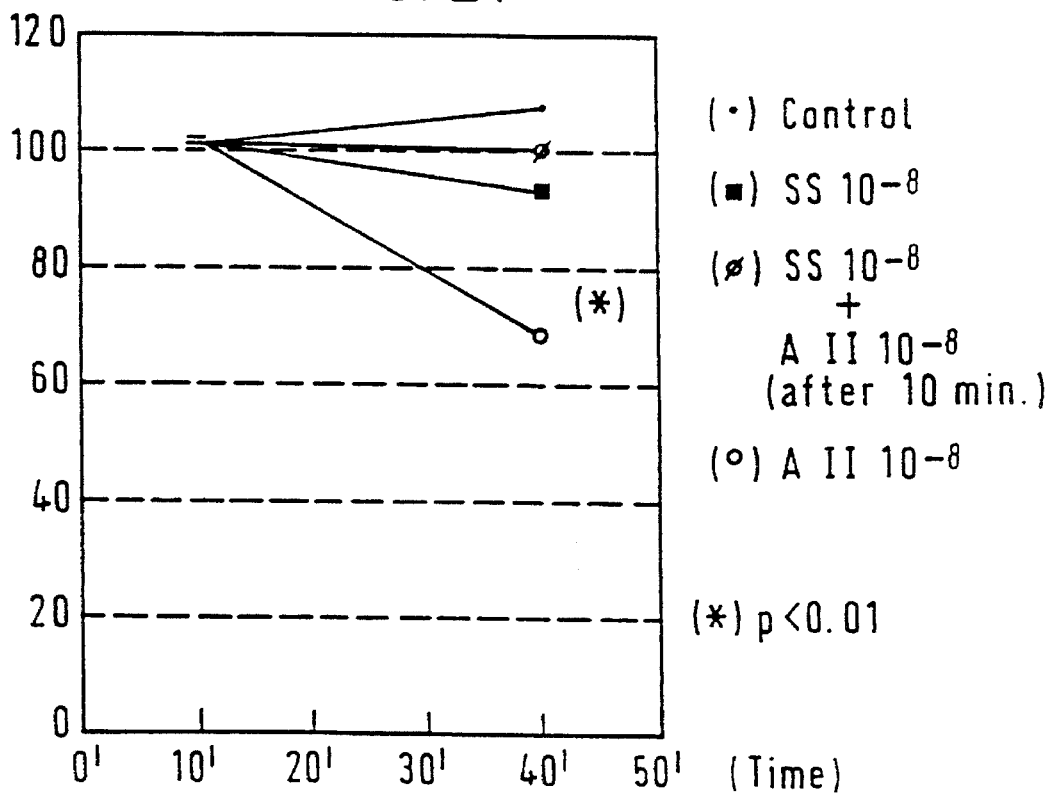

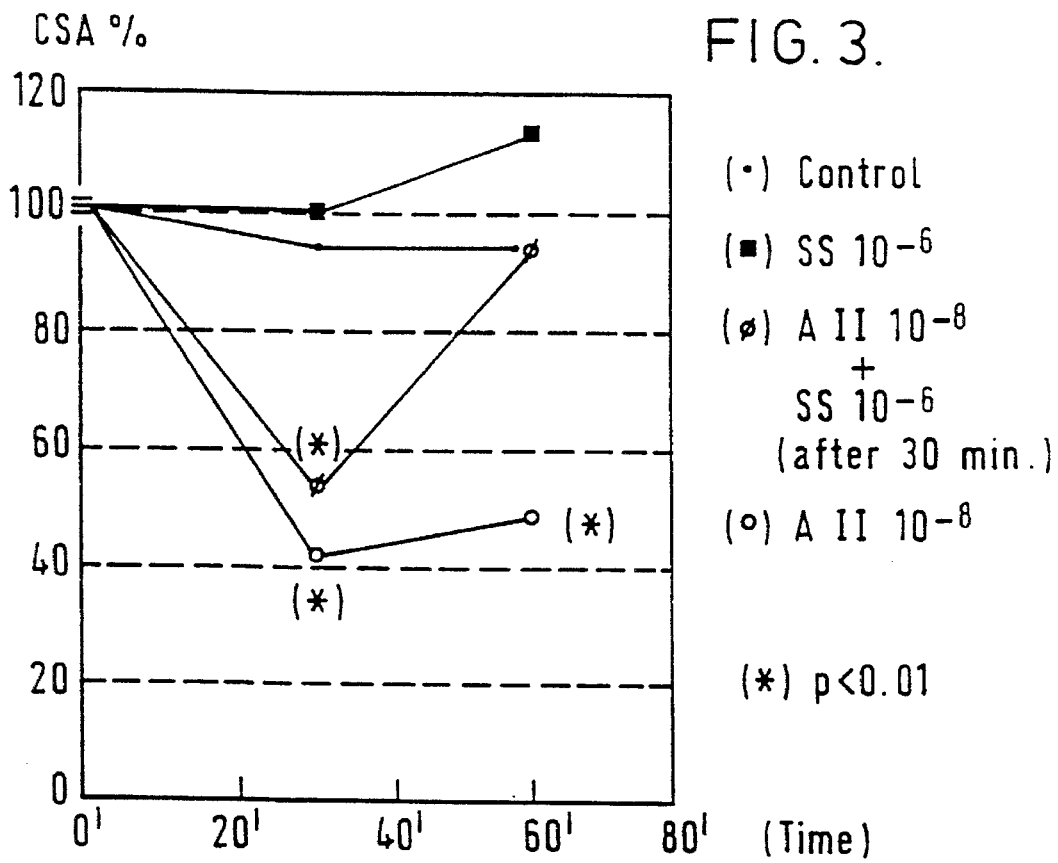
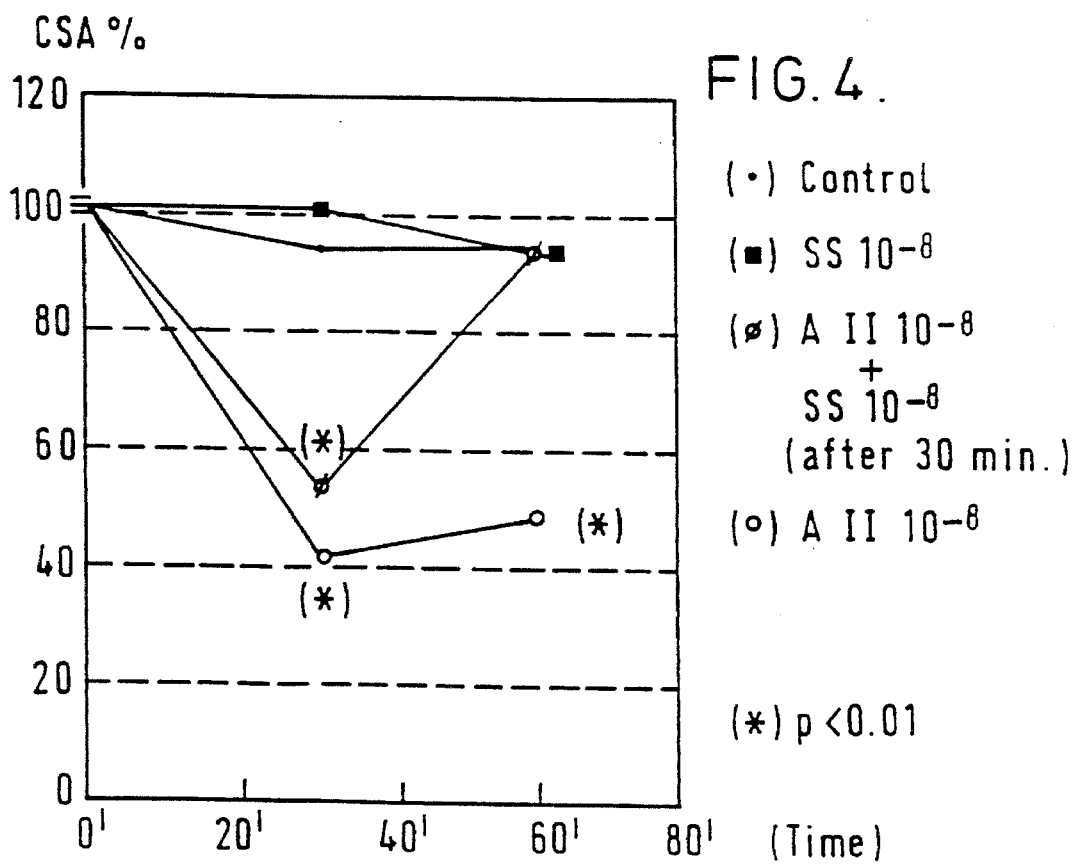

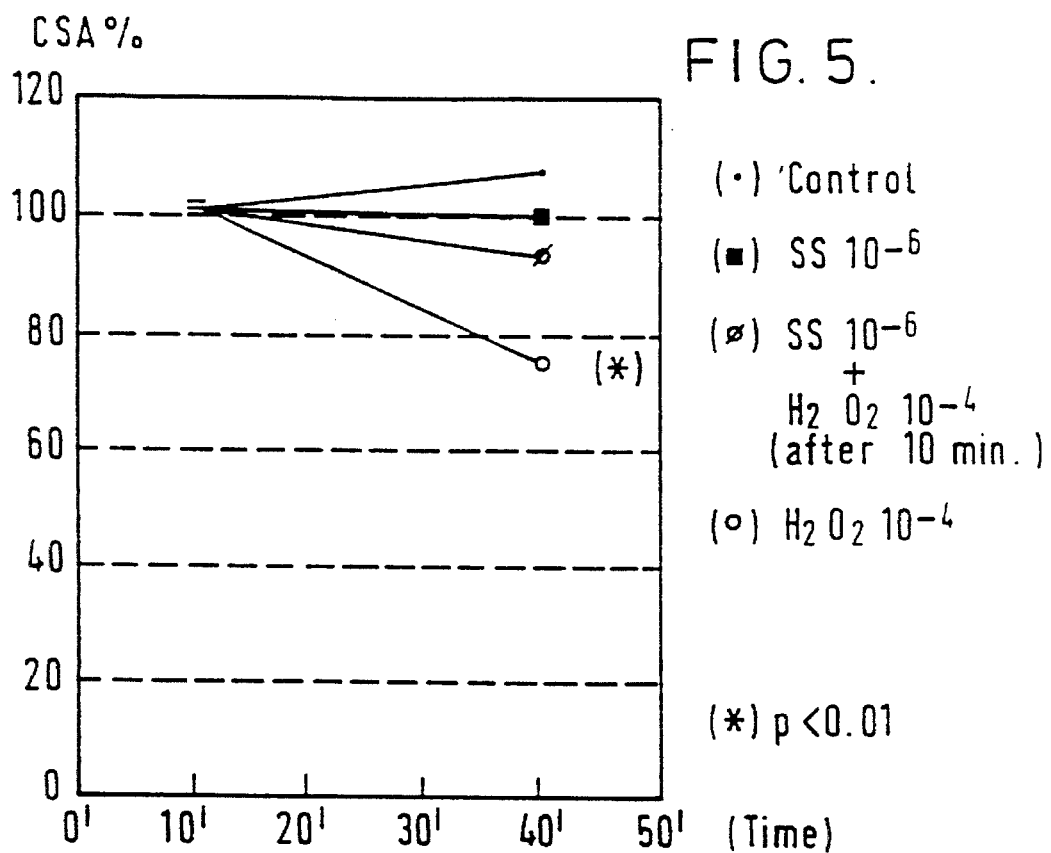
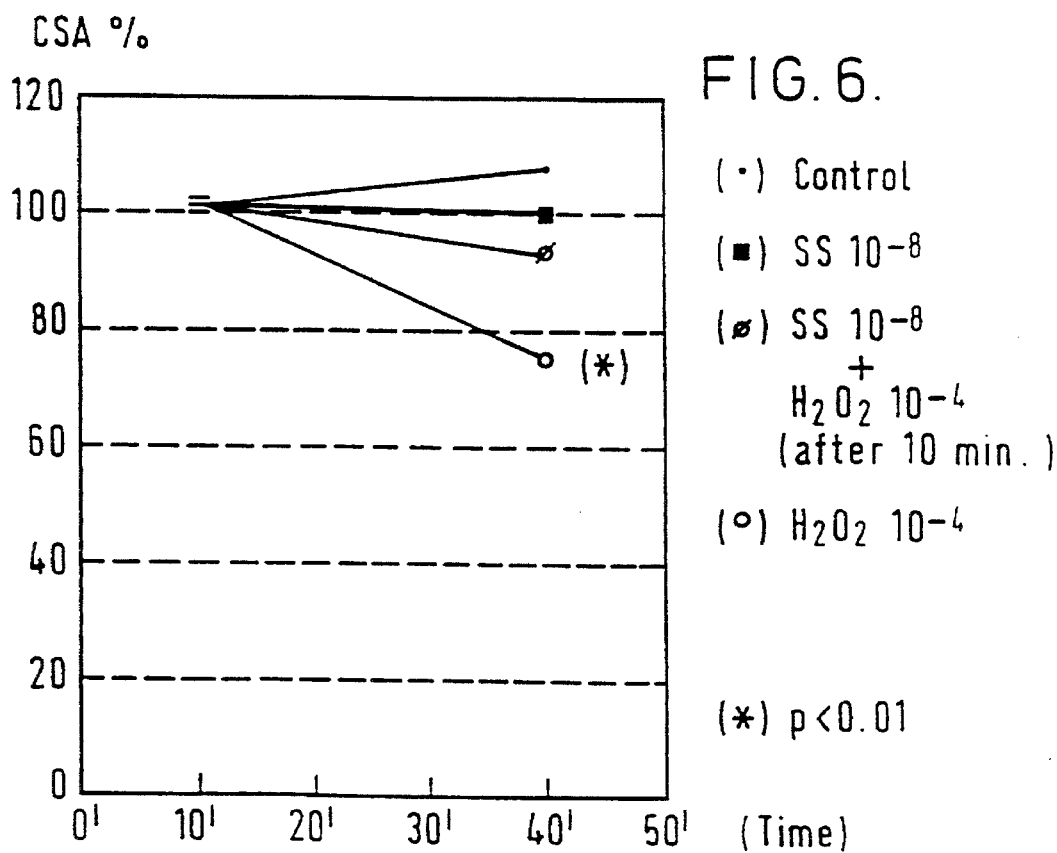

SOMATOSTATIN-ACTIVE POLYPEPTIDE COMPOSITION

This application is a continuation of application Ser. No. 07/623,943, filed Oct. 6, 1990, now abandoned.

This invention relates to chemical compounds and their use in medicine and to pharmaceutical compositions containing such compounds.

Somatostatin (also known as growth-hormone-release-inhibiting hormone GHRIH and somatotrophin-release-inhibiting factor) is a peptide which is fourteen amino acid residues in length, usually with an internal disulphide linkage between the cysteine residues at positions 3 and 14 in the naturally occurring form. The naturally occurring form can be isolated from the hypothalamus. Somatostatin has been produced by synthesis and then usually has a linear form. Clinically, somatostatin has been used in the treatment of patients suffering from acromegaly, caused by elevated levels of circulating growth hormone. Various studies have suggested that somatostatin may have a role in the regulation of pancreatic, duodenal, and gastric secretions (see for example Sizonenko, P.C., Postgrad. Med. J. 1978, 54 suppl. 1, 91).

It has been shown by H. Ashton et al (Br. J. Clin. Pharmac. 1976, 3 523) that somatostatin infusions of 250 to 375 microgrammes can cause a reduction in heart rate of about 10 beats per minute.

An in vitro study by L. Iverson et al (Nature 1978, 273 161) suggested that somatostatin may act as a neurotransmitter or modulator in the rat brain.

It has been suggested by P. E. Lins et al (Lancet 1978 2 687) that somatostatin reduces and may aid regulation of urinary calcium excretion.

Other workers have found that somatostatin can increase intracellular cGMP concentrations in some cell types by activating guanylate cyclase.

The action of intracellular cGMP is not completely known but it has been suggested that can antagonise intracellular calcium levels or inhibit calcium-activated cellular pathways.

Somatostatin has been shown to have an effect on blood sugar levels and coagulation (J. E. Gerish, Archs. intern. Med. 1977 137 659 and G. M. Besser et al Lancet 1975 1 1166 respectively), and also to have an effect on pancreatic disorders such as non-malignant insulinomas (S. E. Christensen et al Lancet, 1975 1 1426) and pancreatitis (B. Limberg and B. Kommerell New Engl. J. Med. 1980 303 284).

Somatostatin has a very short duration of action. Accordingly much work has been carried out to produce analogues which have prolonged somatostatin activity as well as making its inhibitory effects more specific, Examples of such analogues are disclosed in U.S. Pat. No. 4728638 (Bauer et al) and DE 3424279 (Sandoz). In these documents it is suggested that the compounds will be useful in the treatment of disorders with an aetiology associated with excess growth hormone-secretion, and that they may be used to treat gastrointestinal disorders, such as acute pancreatitis, as well as some dermatological diseases, e.g. psoriasis, and Alzheimer-type senile dementia.

We have discovered that somatostatin-active polypeptides can prevent or reverse pathological contraction of mesangial cells and other contractile cells responsive to angiotensin and/or oxygen free radicals, and can thus be used to treat or prevent diseases and dysfunctions associated with such contraction, in particular renal dysfunction.

The diseases and dysfunctions caused by mesangial cell contraction include acute renal failure caused by haemodynamic changes such as shock (hypovolemic, cardiogenic or sepsis) or renal ischemia and by acute pancreatitis. Such acute renal failure may, of course, occur in respect of a transplanted kidney where reperfusion-ischemia may be the cause of failure.

Patients suffering from acute pancreatitis often present the additional symptom of acute renal failure, the aetiology being raised by circulating levels of angiotensin II and/or reactive oxygen species, such as peroxides, which lead to vaso-constriction and renal damage.

The nephrotoxic effects of many immuno-suppressive and cytotoxic drugs, such as aminoglucosides and cylosporin, and the nephrotoxic effect of heavy metals and radiological contrast agents, may also be reduced by the administration of somatostatin.

Studies indicate that some forms of glomerulonephritis are caused by mesangial contraction and likewise these diseases maybe treated according to the invention.

The expression "somatostatin-active polypeptides" should be taken to include naturally occurring somatostatins regardless of animal species origin (e.g. bovine, porcine etc), fragments of these somatostatins, recombinantly produced somatostatins and fragments thereof including site-mutagenised peptides, chemically sythesised analogues or truncated and/or modified analogues as well as salts and complexes of the polypetides where formed, providing they exhibit somatostatin-like activity.

The expressions "somatostatin-active" or "somatostatin-like activity" are intended to encompass compounds which broadly exhibit the major pharmacological properties of somatostatin but not necessarily all the properties of somatostatin. Also, each of those properties need not be exhibited to the same degree as exhibited by natural somatostatin. Primarily, they should exhibit the property of preventing cell contraction caused by angiotensin II and/or oxygen free radicals.

Examples of compounds which have somatostatin-like activity include naturally occurring somatostatins and somatostatin analogues as disclosed in U.S. Pat. No. 4728638 and DE 3424279 which are incorporated herein by reference. A preferred analogue is sandostatin, an octapeptide which has been used in the treatment of rheumatoid arthritis.

BRIEF DESCRIPTION OF THE DRAWINGS

FIG. 1 shows the effects of somatostatin on mesangial rat cells in culture, at a concentration of $10^{-6}$M.

FIG. 2 shows the same effects, at a concentration of $10^{-8}$M.

FIG. 3 shows reversal of the contractile effect of angiotensin by addition of somatostatin to the incubation medium, at a concentration of $10^{-6}$ M, 30 minutes after the addition of angiotensin.

FIG. 4 shows again that a hundredfold decrease in somatostatin concentration to $10^{-8}$M produces exactly the same effect as at $10^{-6}$M.

FIGS. 5 and 6 show the effect of hydrogen peroxide on CSA, with and without preincubation with somatostatin concentrations of $10^{-6}$M and $10^{-8}$M, respectively.

FIG. 5 shows the effects of the addition somatostatin at $10^{-6}$M, 30 minutes after the addition of hydrogen peroxide to the cell culture.

Figure 7:
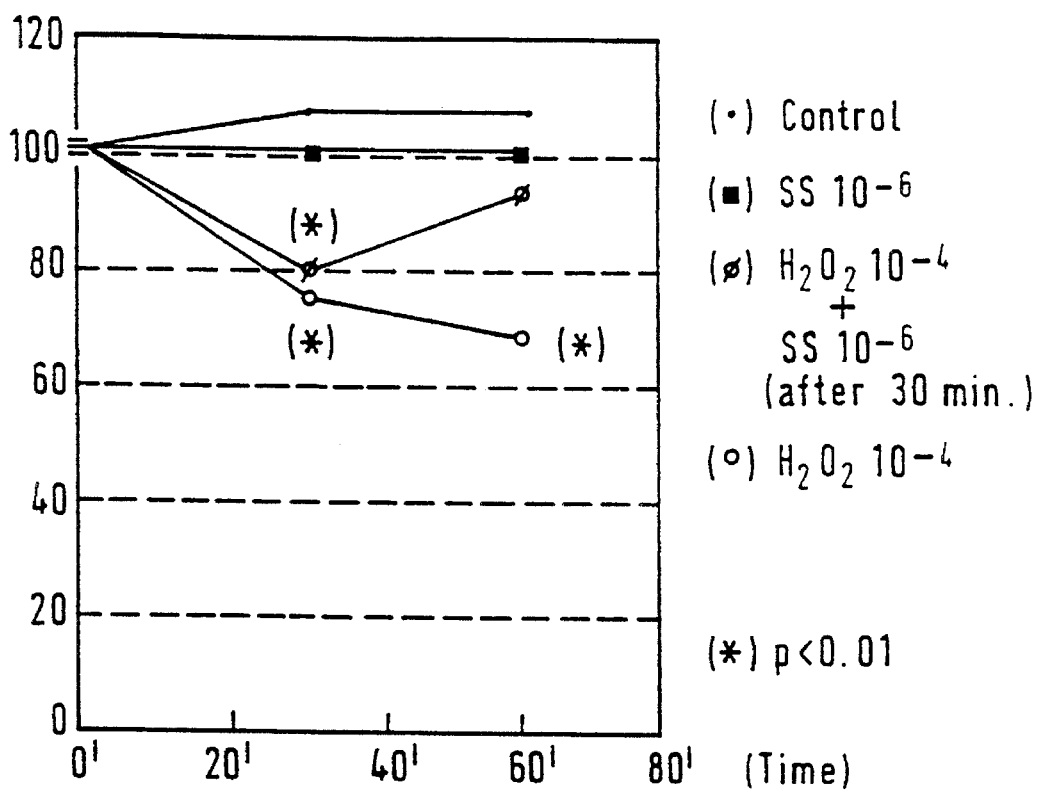

The invention includes pharmaceutical compositions for use in the prevention or treatment of diseases and dysfunctions associated with pathological contraction of mesangial cells and other contractile cells responsive to angiotensin II and/or oxygen free radicals, comprising as active ingredient one or more somatostatin-active polypeptides.

The invention also includes the use of somatostatin-active polypeptides for the preparation of such pharmaceutical compositions.

The compositions may be administered by the oral, rectal, intranasal, transdermal and parenteral routes, the latter being preferred. The proposed dosage is 1 to 500, preferably 20 to 250 mg of active substance per dose, low doses being appropriate for infusion or injection and higher doses being appropriate for other forms of administration. The recommended dose for intravenous application is from 10 to 150 micrograms/Kg/day, preferably from 15–70 micrograms/Kg/day. Where the active substance is administered gradually, for example by infusion, the rate of administration is preferably from 1 to 15 micrograms/kg/hour, more preferably 1.5 to 7 micrograms/kg/hour. Delayed release oral forms should desirably release the active substance at about this dose rate.

3.0 mg of somatostatin may be provided as a daily dose for an individual having a bodyweight of about 80 kg. The somatostatin maybe provided in approximately 2 ml of sterile aqueous medium for bolus intravenous injection. Alternatively, it may be provided in a lyophilised form, with or without an acceptable buffer salts, such as phosphate buffer salts, together with a vial of sterile medium for re-suspension. The somatostatin may also be provided as a sterile aqueous solution for infusion; administration of such an infusion maybe given between four and twenty four hours daily maintaining the treatment as a function of the clinical response.

Suitable forms for administration include tablets, capsules, suppositories, solutions, syrups, emulsions, aerosols and dispersible powders. Suitable tablets may be prepared, for example, by mixing the active substance or substances with known adjuvants, for example inert diluents such as calcium carbonate, calcium phosphate or lactose, disintegrants such as corn starch or alginic acid, binders such as starch or gelatine, lubricants such as magnesium stearate or talc and/or agents for obtaining delayed release such as carboxypolymethylene, carboxymethylcellulose, cellulose acetate phthalate or polyvinyl acetate. The tablets may also consist of several layers.

Coated tablets may be prepared in the same way by coating cores produced analogously to the tablets with substances conventionally used for tablet coating, e.g. collidone or shellack, gum arabic, talc, titanium dioxide or sugar. In order to obtain delayed release or prevent intolerance, the core may also consist of several layers. Similarly, the tablet coating may consist of several layers in order to achieve delayed release, using the excipients given above for the tablets.

In order to avoid degradation of the active polypeptide by gastric acids, tablets may be provided with an enteric coating which is insoluble at the pH in the stomach but dissolves at the pH of the intestine e.g. pH 6.0 or greater. Suitable coating materials include polymethylemthacrylates such as Eudragit (Röhm, Darmstadt).

Syrups of the active substances or combinations of active substances according to the invention may additionally contain a sweetener such as saccharin, cyclamate, glycerine or sugar and a flavour-enhancing agent, e.g. a flavouring such as vanillin or orange extract. They may also contain suspension adjuvants or thickeners such as sodium carboxymethylcellulose, wetting agents, e.g. condensation products of fatty alcohols with ethylene oxide, or preservatives such as p-hydroxybenzoates, Solutions for infusion or injection may be prepared in conventional manner, e.g. with the addition of preservatives such as p-hydroxybenzoates or stabilisers such as alkali metal salts of ethylene-diamine tetraacetic acid and may then be transferred into infusion vessels, injection vials or ampoules. Alternatively, the compound for injection maybe lyophilised either with or without the other ingredients and be solubilised in a buffered solution or distilled water, as appropriate, at the time of use. Bolus intravenous injections may be given.

Capsules containing the active substances or combinations of active substances may be prepared, for example, by mixing the active substances with inert vehicles such as lactose or sorbitol and encapsulating them in gelatine capsules.

Suitable suppositories may be prepared, for example, by mixing with carrier substances provided for this purpose, such as neutral fats or polyethylene glycol or derivatives thereof.

The compound may be mixed with a polylactide or a glutamic acid based copolymer to provide an implantable sustained release delivery system, as described respectively in U.S. Pat. No. 377919 and by K. R. Sidman et al (J. Membrane Sci. 1980 7 277–291).

The invention further includes a method of treatment or prophylaxis of a human or animal subject suffering from or at risk to a disease or dysfunction associated with pathological contraction of mesangial cells or other contractile cells responsive to angiotensin II and/or oxygen free radicals wherein an effective dose of a somatostatin-active polypeptide is administered to said subject.

One of the many factors used to assess renal conditions is glomerular filtration (GF) and the associated coefficient of ultrafiltration (Kf). This coefficient, in turn, is dependent on glomerular permeability and the area of filtration surface. The size of the surface is governed by a variety of factors, but one of the most important is the degree of contraction or relaxation of the mesangial cells situated between glomerular capillary loops. These cells have the property of contracting or relaxing in repsonse to different stimuli; thereby modifying the GF.

Below we provide data on studies carried out on mesangial cells in culture. Cell surface area (CSA) was used as a measure of contraction and relaxation . Variations in CSA may not necessarily involve contraction or relaxation; they may for example be simple changes in cell morphology in two dimensions without their having to involve general contraction. However, it is generally accepted that changes in CSA involve contraction and/or relaxation. This has been confirmed in various ways. Changes in CSA often coincide with an increase in phosphorylation in the light chain of myosin, which is biologically responsible for the contractile effect. Changing cell culture substrates shows that there is a relationship between cell morphology, response and the culture substrate. Moreover, studies of more complex structures, such as glomeruli, alongside mesangial cells, have shown a clear correlation between contractile/relaxing phenomena at cell and glomerulus level. Finally, in many cases, the effects of contraction and relaxation on mesangial cells are closely correlated with changes of glomerular filtration in vivo.

We have found that somatostatin is capable of completely preventing the contractile effect of angiotensin II on rat mesangial cells in culture. The prevention of the contractile effect takes place not only at high somatostatin concentrations, but also at low ones, in the order of $10^{-8}$M, suggesting that the role of somatostatin for this cell type is not only of a pharmacological nature, but also that it has physiological importance. Furthermore, when mesangial cells were contracted by means of a completely different stimulus, such as hydrogen peroxide (providing a reactive oxygen species), somatostatin proved equally effective in preventing the contractile effect of this substance.

We have also found that somatostatin not only has the capacity to prevent angiotensin II or hydrogen peroxide induced cell contraction when mesangial cells are pretreated with somatostatin, but that it is also reverses contraction when it is added after prior incubation of cells with angiotensin II or hydrogen peroxide. This is an extremely important finding as it suggests that somatostatin is effective for reversing contractile effects in pre-contracted cells.

Two types of physiopathological consequences present themselves. Firstly, angiotensin II is an endogenous regulator of peripheral vascular resistance and of aldosterone synthesis. In this respect, it is an important regulator of arterial pressure. Furthermore, in recent years the importance of the rennin-angiotensin system has been clearly shown in the regulation of local blood flow at specific organ level. This is especially important and is known at kidney level, where angiotensin II generated in situ is capable of modifying kidney blood flow and GF and of reducing them. GF does not usually decrease significantly in the presence of angiotensin II, as there are compensating mechanisms that counteract its effects. However, in the presence of other possible changes, such as inhibition of prostaglandin synthesis or the presence of immunological and toxic stimuli, angiotensin II is capable of reducing glomerular filtering significantly. This proves of particular importance in situations of depletion of extracellular volume. In this context, the physiological response of the kidney, amongst others, is a stimulation of the production of rennin, with the subsequent increase in the synthesis of angiotensin II. In these conditions, any extra stimulus may bring about a deterioration in kidney function. Such as acute kidney failure associated with a major depletion in volume. In these circumstances the antagonising effect of angiotensin II at mesangial cell level may be particularly beneficial, as deterioration of the kidney would not take place.

In the case of free radicals, the considerations are similar to those of angiotensin II, although the context in which a modification in glomerular function occurs in connection with free radicals is different. It appears that the free .radicals may intervene in the reduction of glomerular filtrate associated with specific renal pathologies, such as certain types of glomerulonephritis or the use of certain nephrotoxic drugs. What is more, it has been suggested that in situations of renal ischemia, as with other ischemias, an increase in the production of free radicals arises that is responsible, at least in part, for kidney damage. Our studies have shown that one of the mechanisms by which these free radicals determine a reduction in glomerular filtration is through a contraction of the mesangial cells. Somatostatin, however, counteracts this contractile effect of the free radicals on these cells.

Considering all these effects as a whole, led to the conclusion that somatostatin will prove particularly useful in situations typified by significant depletion in blood volume, with secondary activation of the rennin-angiotensin system, and by an increase in the production of toxic free radicals. An important situation in which these phenomena of activation of the rennin-angiotensin-aldosterone system and increase in the production of free radicals are physiopathologically significant is pancreatitis. Human and experimental pancreatitis are characterised by necrosis and inflammation of pancreatic tissue accompanied by various physiological changes. These include a depletion in intravascular volume, with subsequent activation of the rennin-angiotensin system, and an increase in the production of systemic oxidative phenomena, probably as a result of the hyperproduction of free radicals. In these circumstances, it is not surprising that patients with pancreatitis quite often have kidney failure to a greater or lesser degree. Treatment with somatostatin, which counteracts the effects of angiotensin II and of free radicals at mesangial cell level, may prove effective in preventing a reduction in GF and thereby improve recovery of these patients.

From a clinical point of view, one of the most important aspects of these results is the capacity of somatostatin to prevent and to reverse the contractile effect of angiotensin II and of hydrogen peroxide. This means that somatostain may be used both as a preventive and as therapeutic agent, making it possible not only to prevent the appearance of kidney damage in those cases where this condition may be expected, but also enabling this condition to be treated in cases of prior intervention. Again in the case of pancreatitis, our results suggest that, after establishing careful criteria of kidney failure risk or even detecting it in its early stages, the administration of somatostatin could prove beneficial for patients and forestall kidney complications that may prove fatal in many cases.

The ability of somatostatin to reverse contraction of mesangial cells suggests that its use will also extend to the protective treatment of kidneys for transplantation.

EXAMPLES

The invention will now be described by reference to our experimental work and to non-limiting examples of pharmaceutical compositions produced in accordance with the invention.

In the drawings, the experimental data are shown graphically in FIGS. 1 to 8 and examples of micro-photographs from which data were collected are given in FIGS. 9 to 12.

The mesangial cells were obtained after glomeruli isolation by differential sieving (R. P. Misra. Am. J. Clin. Pathol 1972 58 135–139) and collagenase digestion of kidney tissue from Wistar rats. The cell surface area (CSA) was measured using a digital planimeter.

In experiments concerned with the ability of somatostatin to prevent contraction, the mesangial cells were incubated with somatostatin for ten minutes at a concentration of $10^{-6}$M or $10^{-8}$M before the addition of angiotensin II ($10^{-8}$M) or hydrogen peroxide ($10^{-4}$M).

In experiments concerned with the ability of somatostatin to revese contraction, the mesangial cells were incubated for 30 minutes with either angiotensin II or hydrogen peroxide (at the concentrations mentioned above) before somatostatin at a concentration of $10^{-6}$M or $10^{-8}$M was added to the cells.

In all these experiments, control cells lacked the addition of somatostatin, angiotensin II or hydrogen peroxide to the buffer.

Microphotographs were taken at different times and the CSA measured. Each experiment was repeated three times and a total of 8–15 cells were measured for each part of each experiment. The results are expressed as a percentage increase or decrease over the initial CSA, multiplied by 2.

PREVENTION AND REVERSAL OF ANGIOTENSIN II INDUCED CONTRACTION

FIG. 1 shows the effects of somatostatin on the mesangial rat cells in culture, at a concentration of $10^{-6}$M. We observed no significant effect in isolation of this substance on the CSA of this cell type. On the other hand, angiotensin was capable of significantly reducing the CSA after 30 minutes incubation. Preincubation for 10 minutes with somatostatin completely inhibited the contractile effect of angiotensin on mesangial cells. FIG. 2 shows that the same effect occurs when the dose of somatostatin was reduced by a factor of a hundred to $10^{-8}$M.

FIG. 3 shows that the addition of somatostatin, at a concentration of $10^{-6}$M, reverses the contractile effect of angiotensin despite being added to the incubation medium 30 minutes after the addition of angiotensin. We did not observe any significant change in CSA of the control cells or in those incubated in isolation with somatostatin. FIG. 3 also shows that angiotensin induced contraction persisted for 60 minutes.

FIG. 4 shows again that a hundredfold decrease in somatostatin concentration to $10^{-8}$M produces exactly the same effect as at $10^{-6}$M.

PREVENTION AND REVERSAL OF HYDROGEN PEROXIDE INDUCED CONTRACTION

Hydrogen peroxide induced a significant reduction in CSA at the concentration used. This effect was prevented by preincubation with somatostatin at concentrations of $10^{-6}$M (FIG. 5) or $10^{-8}$M (FIG. 6). In both experiments, somatostatin did not in itself induce any significant change in CSA compared with the control.

Figure 8:
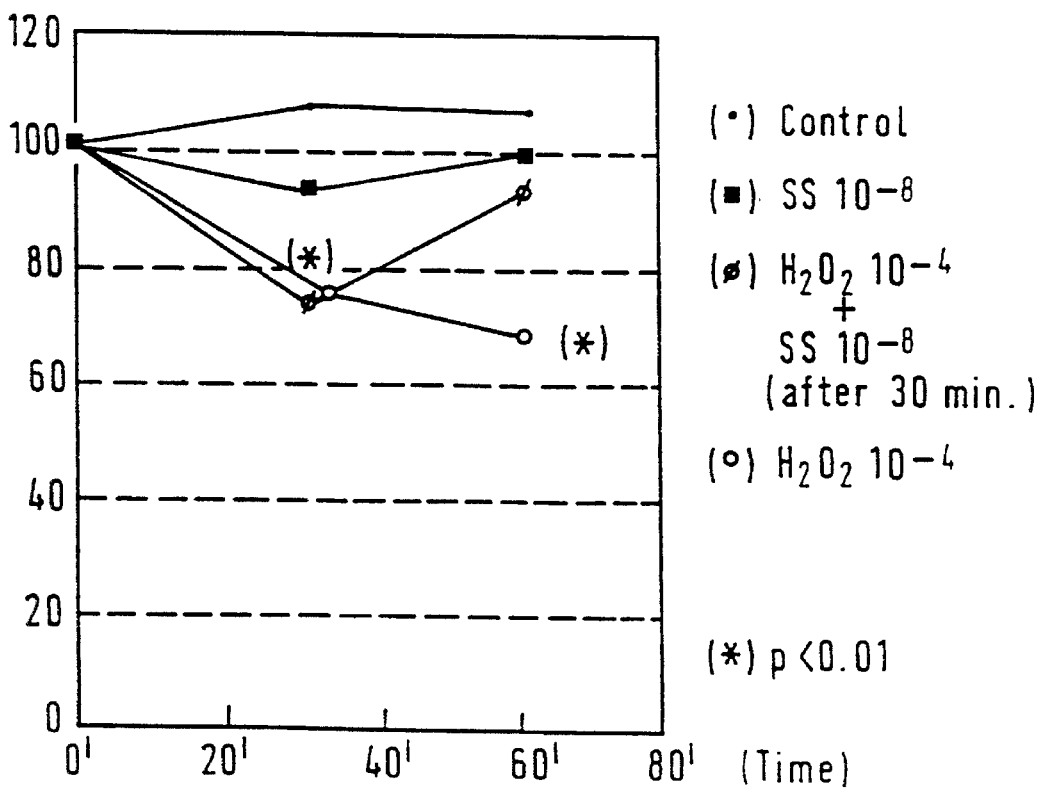
FIG. 8 shows the effects of the addition somatostatin at $10^{-8}$M, 30 minutes after the addition of hydrogen peroxide to the cell culture.

Reversal of the contractile effect of hydrogen peroxide on mesangial cells, occurred with somatostatin at both concentrations. FIG. 7 shows the effects of the addition somatostatin at $10^{-6}$M, 30 minutes after the addition of hydrogen peroxide to the cell culture. It can be seen that the CSA returns to normal after a further 30 minutes. Cells treated with hydrogen peroxide but without somatostatin remained in a contracted state. The same effect was demonstrated with somatostatin at a concentration of $10^{-8}$M (FIG. 8). In both cases somatostatin did not significantly effect CSA when add to untreated cells, whereas hydrogen peroxide induced contraction persisted in cells treated with only hydrogen peroxide.

Figure 9A:
FIGS. 9A, 9B and 9C show microphotographs of mesangial cells of a control group at t=0, t=30 and minutes, respectively.
Figure 9B:
Figure 9C:
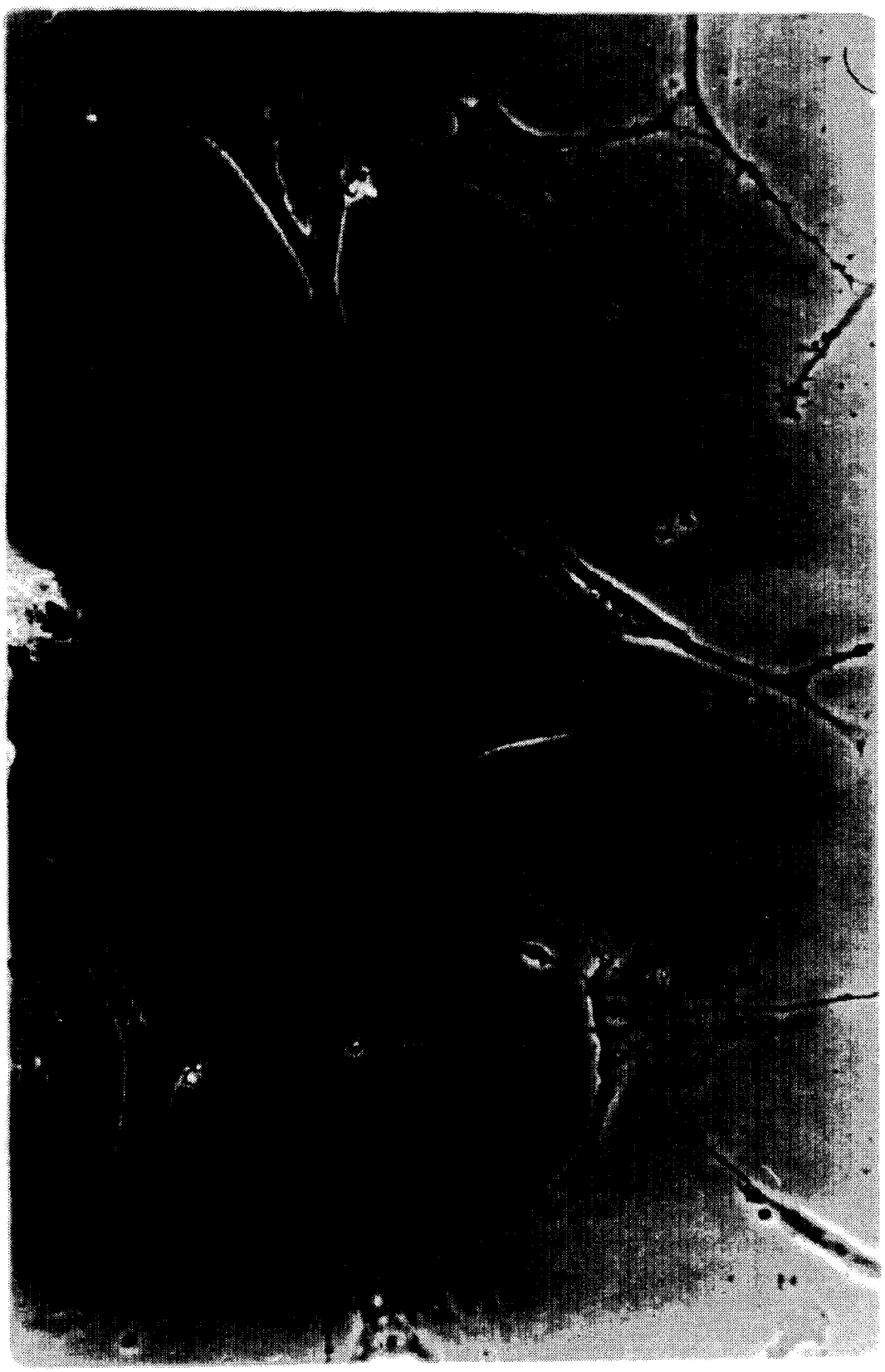

FIGS. 9A, B and C show microphotographs of mesangial cells of a control group at t=0, t=30 and t=60 minutes respectively. It can be seen that the cells show little sign of changes in shape.

Figure 10A:
FIGS. 10A, 10B and 10C show microphotographs of mesangial cells treated with hydrogen peroxide.

FIGS. 10A, B and C show microphotographs of mesangial cells treated with hydrogen peroxide. The microphotographs show the cells at t=0, t=30 and t=60 minutes respectively. It can be seen that the cells, e.g. those marked by arrows, have contracted to a significant degree.

Figure 10B:
Figure 10C:
Figure 11A:
FIGS. 11A, 11B and 11C show micrographs of mesangial cells treated with hydrogen peroxide and then treated at t=0, t=30, and t=60 minutes, respectively with somatoetatin.
Figure 11B:
Figure 11C:
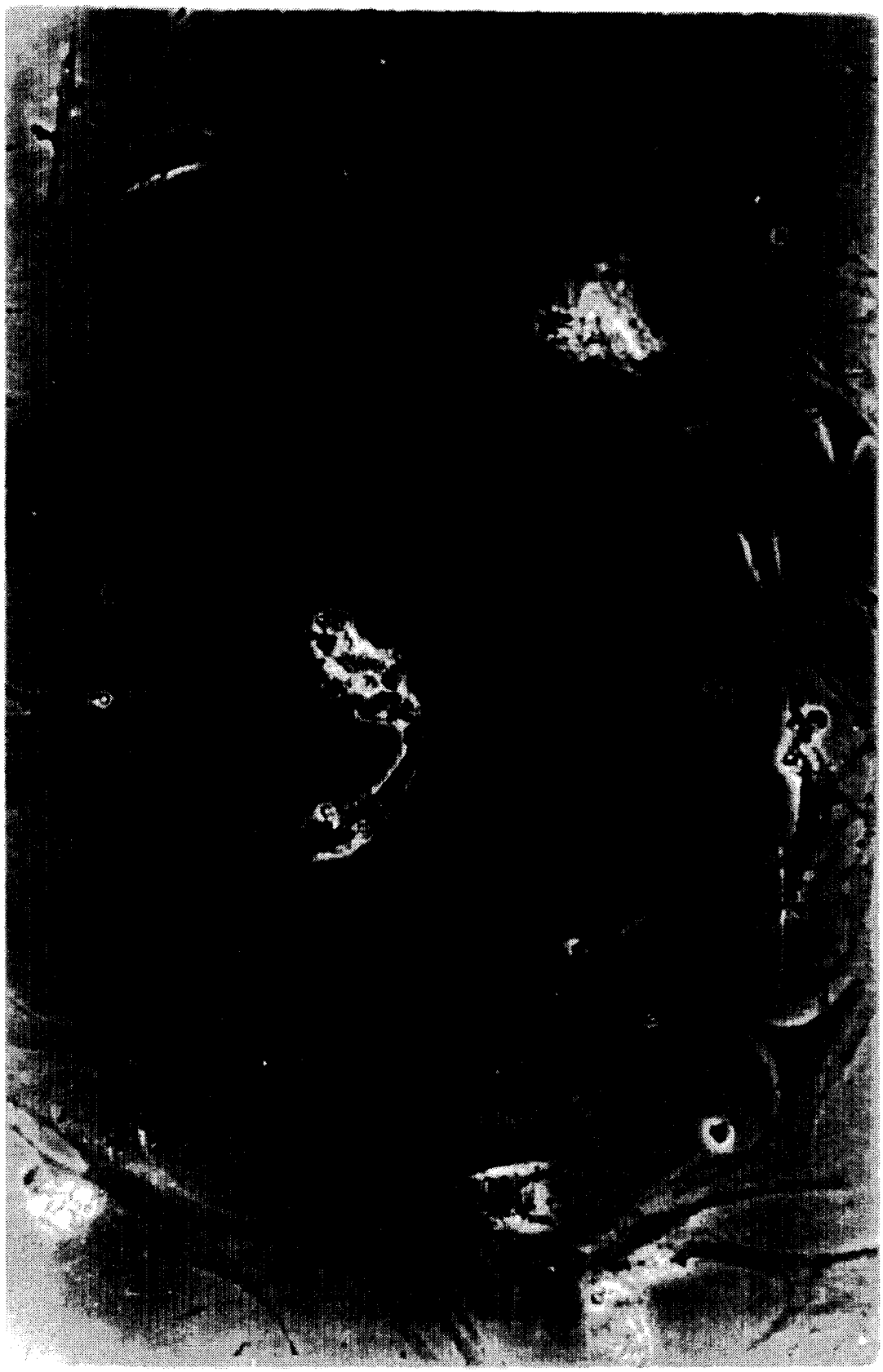

In contrast to FIG. 10, FIG. 11 shows micrographs of mesangial cells treated with hydrogen peroxide and then treated at t=30 minutes with somatostatin. FIGS. 11A, B and C were taken at t=0, t=30 and t=60 minutes respectively. It can be seen that cells, e.g. The cell arrowed, contract between t=0 and t=30 minutes under the action of hydrogen peroxide. At t=30 somatostatin was added and the cells relax to almost their original size by t=60 minutes.

It should be noted that figures such as FIGS. 10 and 11 were used to provide data for FIGS. 7 and 8.

Figure 12A:
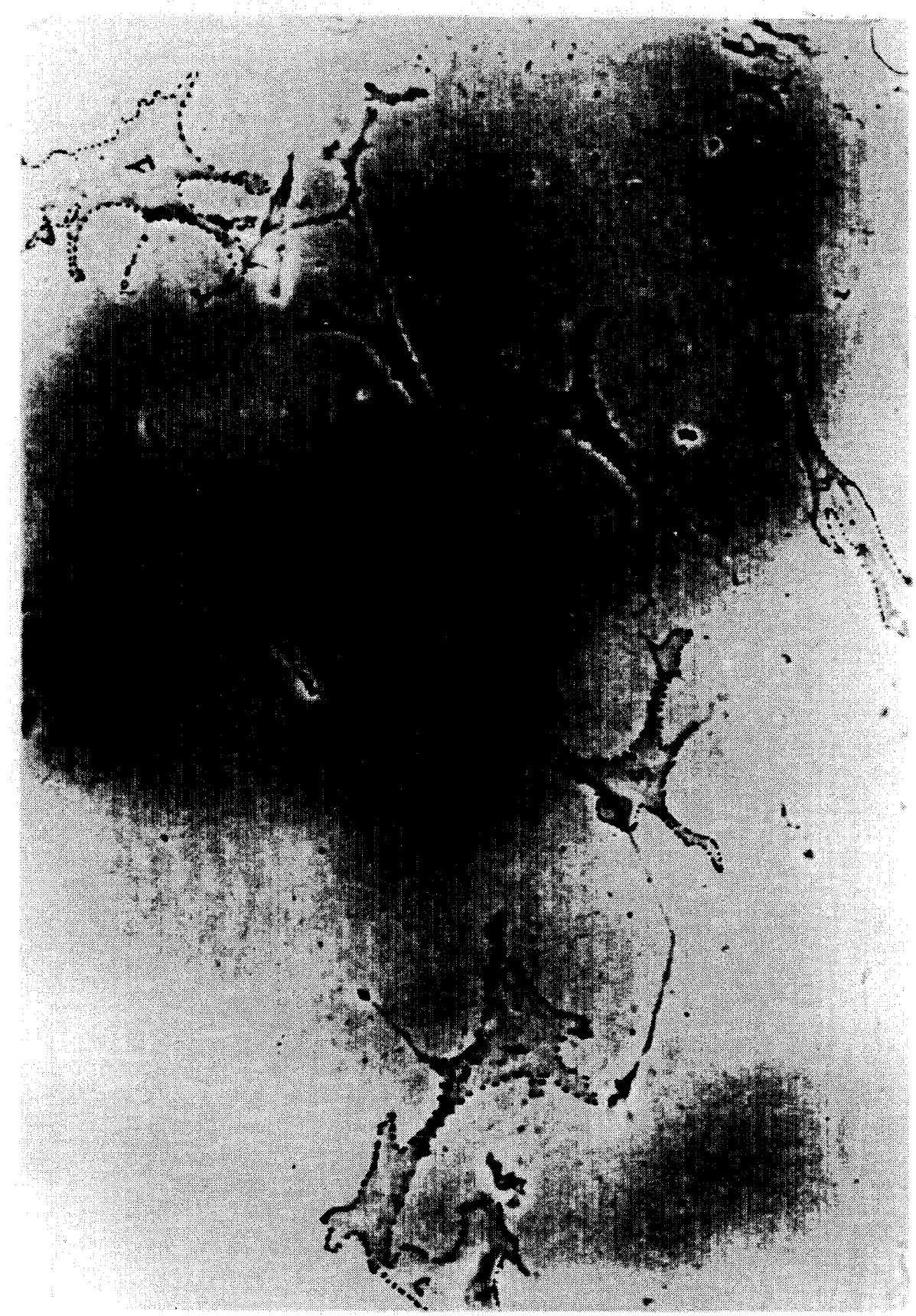
FIGS. 12A and 12B show microphotographs of cells pre-treated with somatostatin before the addition of angiotenein II as described in relation to FIGS. 1 and 2.
Figure 12B:

FIGS. 12A and B show microphotographs of cells pretreated with somatostatin before the addition of angiotensin II as described in relation to FIGS. 1 and 2. It can be seen that there is substantially no change in the size of these cells.

We claim:

1. A method of prophylaxis of a human or animal subject at risk of renal dysfunction, said dysfunction being associated with a pathological contraction of mesangial cells responsive to angiotensin II and/or oxygen free radicals, which comprises the step of:

administering a somatostatin-active polypeptide to said subject in a dose effective to prevent said pathological contraction of mesangial cells, wherein said dose is from 10–150 µg/kg/day.

2. A method according to claim 1 in which the somatostatin-active polypeptide is a natural or recombinant somatostatin or active fragment thereof or a pharmaceutically acceptable salt or complex thereof.

3. The method of claim 2, wherein said somatostatin-active polypeptide is a natural or recombinant somatostatin, or a pharmaceutically acceptable salt thereof.

4. A method according to claim 1, wherein said effective dose is 15–50 µg/kg/day.

5. A method of treatment of a human or animal subject suffering from renal dysfunction, said dysfunction being associated with pathological contraction of mesangial cells responsive to angiotensin II and/or oxygen free radicals which comprises the step of:

administering a somatostatin-active polypeptide to said subject in a dose effective to reverse said pathological contraction of mesangial cells, wherein said dose is from 10–150 µg/kg/day.

6. A method according to claim 5 in which the somatostatin-active polypeptide is a natural or recombinant somatostatin or active fragment thereof or a pharmaceutically acceptable salt or complex thereof.

7. The method of claim 6, wherein said somatostatin-active polypeptide is a natural or recombinant somatostatin, or a pharmaceutically acceptable salt thereof.

8. The method of claim 5, wherein said disfunction is caused by a factor selected from the group consisting of hemodynamic changes, glomerulonephritis, an immunosuppressive drug, and a cytotoxic drug.

9. The method according to claim 8, wherein said factor is selected from the group consisting of glomerulnephritis, an immunosuppressive drug and a cytotoxic drug.

10. A method according to claim 5, wherein said factor is glomerulonephritis.

11. A method according to claim 5, wherein said factor is an immunosuppressive drug.

12. A method according to claim 5, wherein said factor is a cytotoxic drug.

13. A method according to claim 5, wherein said effective dose is 15–50 µg/kg/day.

* * * * *